US005633028A

United States Patent [19]

Wong

[11] Patent Number: 5,633,028
[45] Date of Patent: May 27, 1997

[54] FAST HYDRATING DUST-FREE XANTHAN GUM

[75] Inventor: Philip Wong, Kendall Park, N.J.

[73] Assignee: Rhone-Poulenc Inc., Cranbury, N.J.

[21] Appl. No.: 644,595

[22] Filed: May 10, 1996

Related U.S. Application Data

[63] Continuation of Ser. No. 168,264, Dec. 14, 1993, abandoned.

[51] Int. Cl.$^6$ .................................................. A23L 1/054
[52] U.S. Cl. ................... 426/99; 426/302; 426/573
[58] Field of Search .......................... 426/99, 573–579, 426/302

[56] References Cited

U.S. PATENT DOCUMENTS

| | | | |
|---|---|---|---|
| 3,146,200 | 8/1964 | Goldstein et al. | 252/8.5 |
| 3,801,502 | 4/1974 | Hitzman | 252/8.55 |
| 3,912,713 | 10/1975 | Boonstra et al. | 260/209 |
| 4,041,234 | 8/1977 | Maske | 536/114 |
| 4,057,509 | 11/1977 | Costanza et al. | 252/316 |
| 4,218,262 | 8/1980 | Warren | 106/206 |
| 4,254,257 | 3/1981 | Schroeck | 536/52 |
| 4,260,741 | 4/1981 | Schuppner, Jr. | 536/114 |
| 4,269,974 | 5/1981 | Wintersdorff | 536/114 |
| 4,278,692 | 7/1981 | Cassanelli | 426/96 |
| 4,299,825 | 11/1981 | Lee | 424/180 |
| 4,363,669 | 12/1982 | Cottrell et al. | 106/205 |
| 4,654,086 | 3/1987 | Baird et al. | 106/205 |
| 5,003,060 | 3/1991 | Vinot | 536/114 |
| 5,224,988 | 7/1993 | Pirri et al. | 106/208 |
| 5,270,459 | 12/1993 | Shatzman et al. | 536/114 |

*Primary Examiner*—Jeanette Hunter
*Attorney, Agent, or Firm*—Andrew M. Solomon

[57] ABSTRACT

A xanthan gum composition is prepared that is useful as a thickener and suspension agent in food and pharmaceutical applications. Comprised of xanthan gum and small amount of a food grade emulsifier, the composition is both shelf stable, dust-free and fast hydrating thereby providing a product that is easily assimilated into its end product uses with fewer steps and costs of manufacture.

13 Claims, 1 Drawing Sheet

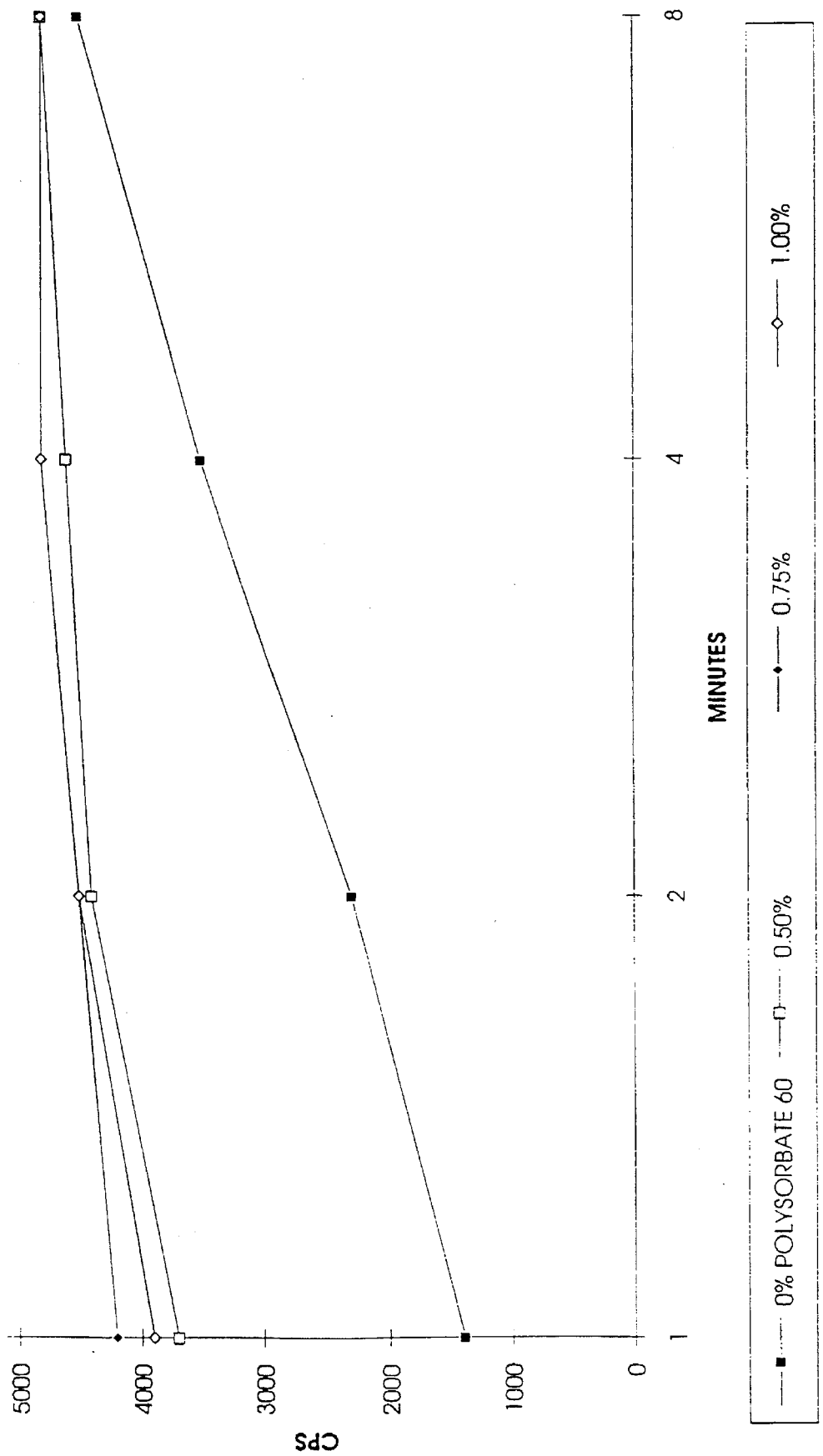

FAST HYDRATING DUST-FREE XANTHAN GUM

This application is a continuation of application Ser. No. 08/164,264, filed Dec. 14, 1993, now abandoned.

BACKGROUND OF THE INVENTION

Xanthan gum is a synthetic, water soluble bipolymer derived from the fermentation of carbohydrates by several bacterial species of the genus Xanthomonas and is useful as a thickening and suspension agent in numerous applications. It is tolerant in both strongly acidic and basic conditions and is also heat stable, thereby being useful in many chemical, pharmaceutical and, in particular food applications such as dairy products, beverages and high protein foods.

Xanthan gum displays poor wettability properties however and is very difficult to disperse in water and/or hydrate. A high degree of shear is usually necessary to wet each gum particle in order to disperse it into solution. It is preferably produced as a dry particle for ease in storage prior to end use application and therefore it would be advantageous to develop a substantially dry, dust-free xanthan gum composition that is readily hydratable when ready for use.

A xanthan gum composition with a fast hydration rate would be advantageous in that it can be mixed far more readily into the final food or pharmaceutical product. Xanthan gum as is presently available must be agglomerated in order to increase the rate of hydration. This method of processing is expensive and necessitates high capital expenditures. A fast hydrating xanthan gum composition such as that of the present invention will lower the costs of manufacture by avoiding these costly agglomeration procedures. Moreover, a dust-free product is advantageous from a health standpoint by reducing air borne particles which may be inhaled by workers in the industry as well as lessening the risk of explosion during storage and the prevention of loss of product during storage and transport. A dust-free product will also lessen the number of accidents caused by slippery conditions resulting from spillage of the product.

Historically, when a fast hydrating dust-free powder is desired, the process that is used to achieve these benefits is agglomeration. However, this process is expensive and therefore increases the cost of the final product. U.S. Pat. No. 4,041,234 to Maske discloses dispersible glyoxal-xanthan gum complexes in which glyoxal is added to the xanthan gum fermentation broth in order to improve its dispersibility. However, high amounts of glyoxal are required to adequately disperse the fermentation product when added to an aqueous solution. This is not only a costly procedure but the glyoxal affects the taste of the final products.

U.S. Pat. No. 4,299,825 to Lee discloses concentrated xanthan gum solutions of high viscosity using numerous ultrafiltration steps. However, these comprise only from 8% to 15% xanthan gum and as such exists in solution and is not a dust-free hydratable particle. U.S. Pat. No. 4,670,550 to Bleeker et. al. disclose bipolymer emulsions similar to xanthan gum compositions using high shear techniques, while U.S. Pat. No. 4,254,257 to Schroeck discloses the precipitation of amine salts of xanthan gum from the fermentation broth. Finally, U.S. Pat. No. 4,269,974 to Wintersdorff discloses a smooth flowing xanthan composition wherein the gum is homogenized with vegetable oil and water. However, all of these references recognize the need to shear the gum in order to hydrate it.

U.S. Pat. No. 4,218,262 to Warren teaches a non-clumping, delayed action viscosity increasing agent comprised of xanthan gum that is encapsulated with a coating comprised of a fat selected from the group consisting of fatty acids, mono- and diglycerides of fatty acids and a surfactant selected from the group comprising the alkali metal salts of fatty acids, sorbitan fatty acid esters, linear alcohol ethoxylates, sucrose fatty acid esters and mixtures thereof. The surfactant serves to increase the solubility of the coating and promote wetting of the fatty acid onto the particle. The coating itself has a hydrophilic/lipophilic value of 3.0–10.0.

U.S. Pat. No. 4,654,086 to Baird et. al. teaches and claims a dry xanthan gum composition that is allegedly dispersible and hydratable comprising xanthan gum blended with a surfactant such as acetylated monoglycerides, glycerol esters, sorbitan esters and the like. Optionally, sugar is added but the surfactant must be incorporated in amount of at least 5.0% and may be used in amount of up to 20%. The problem that arises however, particularly in food related applications, is that the surfactant possesses an undesirable taste which is discernable at these levels and makes the xanthan gum inappropriate for use in most food products. Below 5%, however Baird et. al. '086 recognizes that problems regarding hydration and dispersibility arise again.

It is an object of the present invention to provide a substantially dust-free stable xanthan gum hydrocolloid powder that is fully hydratable and useful as a thickener and suspension agent. It is a further object of the present invention to provide a substantially dust-free, fully hydratable xanthan gum composition comprising xanthan gum and very low amounts of a food grade surfactant so as to be undetectable in food applications. It is a further object of the present invention to produce a substantially stable, dust-free xanthan gum composition that is fully hydratable and is an effective thickening and suspension agent in food and drug applications.

SUMMARY OF THE INVENTION

A substantially dust-free, hydratable xanthan gum composition provides excellent thickening and suspension properties when added to food and chemical applications. The xanthan gum is also stabilized and will not require a high degree of shear and/or agitation applied thereto in order to get it to disperse evenly in solution. The composition is comprised of a xanthan gum polymer and a small amount of surfactant selected from the group of food grade emulsifiers with high hydrophilic/lipophilic balance (HLB) values such as sorbitan esters, glycerol esters, mono- and di-glycerides and the like.

BRIEF DESCRIPTION OF THE DRAWINGS

FIG. 1 is a comparative line graph comparing the relative hydration rates of three xanthan gum compositions of the present invention with that of xanthan gum alone.

DETAILED DESCRIPTION OF THE INVENTION

Whereas there have been prior attempts at producing a hydratable, xanthan gum powder in the prior art, it has not herebefore been made possible with small amounts of additives and without the need for expensive agglomeration procedures. It has been surprisingly and unexpectedly discovered that by using a specific xanthan gum that is the fermentation product of the species *Xanthomonas campestris* sold under the tradename Rhodigel® (Rhone-Poulenc, Inc. Cranbury, N.J.), a xanthan gum composition can be prepared using only a small amount of surfactant which possesses excellent hydration, thickening and suspension-forming properties.

Without being bound to any theory, whereas xanthan gums of the prior art have globular or ovoid shapes that are smooth surfaced when viewed under a microscope, the xanthan gum employed in the compositions of the present invention displays jagged, rough edges and irregular surfaces. Moreover, although all xanthan gums are characterized chemically as polygalactomannons, the gums useful in the present invention are specifically the sodium salt thereof. These features of the gum may enhance the reaction with the surfactant and result in the composition's surprising and unexpected properties as well as also allow for the use of less surfactant to achieve the stated goals.

The surfactant employed preferably is a food grade emulsifier with a high hydrophilic/lipophilic balance (HLB) value. Such values should range from about 10 to about 16. Suitable emulsifiers preferably have also been approved for use in foods since many of the applications for the present invention reside in the food and drug industries. Preferably, the emulsifier is selected from the group consisting of polyoxyethylene sorbitan esters, sorbitan esters, monoglycerides, diglycerides, lecithin, polyglycerols, sodium stearoyl-2-lactylate, stearyl-2-lactylic acid, polyoxystearates, acetylated monoglycerides and mixtures thereof. Preferably, sorbitan esters and polyoxyethylene sorbitan esters are the emulsifiers of choice.

The emulsifier is combined with the xanthan gum polymer in relatively small amounts, i.e. from about 0.1% to about 3.0% of the total weight of the composition. Preferably, the emulsifier will comprise from about 0.1% to about 1.5% by weight of the total weight of the xanthan gum composition.

It was also surprising and unexpected to find the ease with which the xanthan gum and emulsifier are blended together. The xanthan gum is simply placed in a standard Hobart bowl or other similar container and the emulsifier added thereto. Substantially complete blending was achieved using a paddle mixer at low speed for approximately five minutes. The final product was homogeneous and readily miscible.

The following examples are disclosed to more specifically describe the embodiments of the present invention. They are for illustrative purposes only however, and should not be construed as limiting the spirit and scope of the invention as recited by the claims that follow.

EXAMPLE 1

Four xanthan gum compositions using Rhodigel 80® xanthan gum and Polysorbate 60 (polyoxyethylene sorbitan monostearate) were prepared using the standard mixing procedure set forth above and were compared as to their various viscosity values using a Brookfield Model LVT viscometer spindle #3 set at 12 RPM. The percentages of Polysorbate 60 are based on the total weight of the xanthan gum/emulsifier composition and the viscosities were measured in centipoise units (cps) at four different times.

| % POLY-SORBATE 60 | RHODIGEL FH TEST VISCOSITIES (CPS) | | | |
|---|---|---|---|---|
| | 1 MIN. | 2 MIN. | 4 MIN. | 8 MIN. |
| 0.00 | 1400 LARGE LUMPS | 2300 LARGE LUMPS | 3500 LARGE LUMPS | 4500 LARGE LUMPS |
| 0.50 | 3700 SMALL LUMPS | 4400 SMALL LUMPS | 4600 V. SMALL LUMPS | 4800 NO LUMPS |
| 0.75 | 3900 SMALL LUMPS | 4500 SMALL LUMPS | 4800 NO LUMPS | 4800 NO LUMPS |
| 1.00 | 4200 SMALL LUMPS | 4500 V. SMALL LUMPS | 4800 NO LUMPS | 4800 NO LUMPS |

As shown by the respective viscosity values for the different xanthan gum/Polysorbate 60 compositions, the greater the amount of emulsifier used, the greater the viscosity of the gum composition with the greatest viscosity values realized at emulsifier amounts somewhere between 0.75% wt. % and 1.0 wt. %. Viscosity is also a function of the break-up of the gum particles within the system with the absence of lumps creating the most viscous composition achievable. As can be also seen from the chart, there is a point between the concentrations of 0.75 wt. % and 1.0 wt. % of diminishing return, i.e., regardless of how much more emulsifier is added to the composition, the viscosity no longer increases.

Referring now to FIG. 1, the hydration rates of three xanthan gum/emulsifier compositions of the present invention were compared with a pure xanthan gum composition with no emulsifier added. To determine the hydration rate, viscosity (cps) was plotted as a function of time, again, the greater the number of cps. units, the greater the degree of viscosity and hence the greater the hydration rate. A 1.0% solution was prepared and mixed in a spindle mixer equipped with a 2.5 inch blade set at 1000 r.p.m. As can be clearly seen from the graph, xanthan gum/emulsifier compositions wherein the Polysorbate 60 is present in an amount of between about 0.75% and about 1.0% are the most viscous whereas compositions comprising 0.5% emulsifier closely approximate that and become as viscous at about 8 minutes. The xanthan gum sample by itself displayed viscosity values far below those of the compositions of the present invention for the first four (4) minutes of mixing and it was not until eight (8) minutes had passed that the viscosity approached that of the inventive compositions.

The xanthan gum/emulsifier compositions of the present invention are highly viscous, homogenous in texture and pourable. They are also shelf stable and possess none of the off-tastes found in the compositions of the prior art due to the high levels of surfactant required. These characteristics make the ingredient readily incorporated into numerous food and drug applications and therefore ultimately lower the cost of manufacture while increasing its speed.

What we claim is:

1. A composition comprising a mixture of xanthan gum and a surfactant wherein said surfactant is present in an amount of from about 0.1% to about 3.0% by weight of the total weight of the composition and wherein the xanthan gum is characterized by having jagged, rough edges and irregular surfaces.

2. The xanthan gum composition of claim 1 wherein said xanthan gum is prepared from a fermentation broth comprising the microorganism Xanthomonas campestris.

3. The xanthan gum composition of claim 2 wherein said surfactant is a food grade emulsifier with a high hydrophilic/lipophilic balance value.

4. The xanthan gum composition of claim 3 wherein said HLB value ranges from about 10 to about 16.

5. The xanthan gum composition of claim 4 wherein said emulsifier is selected from the group consisting of polyoxyethylene sorbitan esters, sorbitan esters, acetylated monoglycerides, glycerol esters, lecithin, mono- and di-glycerides, sodium steroyl-2-lactylate, polyglycerol esters, propylene glycol esters, stearyl-2-lactylic acid and mixtures thereof.

6. The xanthan gum composition of claim 5 wherein said emulsifier is selected from the group consisting polyoxyethylene sorbitan esters and sorbitan esters.

7. The xanthan gum composition of claim 6 wherein said surfactant is selected from the group consisting of polyoxyethylene sorbitan monostearate.

8. The xanthan gum composition of claim 1 wherein said emulsifier is present in an amount of from about 0.1% to about 1.5% by weight of the total weight of the composition.

9. The xanthan gum composition of claim 8 wherein the viscosity of 1.0% aqueous solution ranges from about 4200 cps. to about at least 4800 cps.

10. A highly viscous, substantially dust-free xanthan gum composition comprising a mixture of xanthan gum and polyoxyethylene sorbitan monostearate, wherein said polyoxyethylene sorbitan monostearate is present in an amount of from about 0.1% to about 3.0% by weight of the total weight of the composition and wherein the xanthan gum is characterized by having jagged, rough edges and irregular surfaces.

11. The xanthan gum composition of claim 10 wherein the viscosity of a 1.0% solution ranges from about 4200 to about 5000 c.p.s.

12. A composition consisting essentially of a mixture of xanthan gum and a surfactant wherein said surfactant is present in an amount of from about 0.1% to about 3.0% by weight of the total weight of the composition and wherein the xanthan gum is characterized by having jagged, rough edges and irregular surfaces.

13. Food compositions containing a xanthan gum thickener/suspension agent comprising a mixture of xanthan gum and a food grade emulsifier selected from the group consisting of polyoxyethylene sorbitan esters, sorbitan esters, acetylated monoglycerides, glycerol esters, lecithin, mono- and di-glycerides, sodium stearoyl-2-lactylate, polyglycerol esters, propylene glycol esters, stearyl-2-lactylic acid and mixtures thereof, wherein said food grade emulsifier is present in an amount of from about 0.1% to about 3.0% by weight of the total weight of the xanthan gum thickener/suspension agent and wherein the xanthan gum is characterized by having jagged, rough edges and irregular surfaces.

* * * * *